(12) United States Patent
Mousa (10) Patent No.: US 9,655,862 B2
(45) Date of Patent: May 23, 2017

(54) OCULAR NANOFORMULATION AND METHOD OF USE IN ANGIOGENESIS-MEDIATED DISORDERS

(71) Applicant: Shaker A. Mousa, Wynantskill, NY (US)

(72) Inventor: Shaker A. Mousa, Wynantskill, NY (US)

(*) Notice: Subject to any disclaimer, the term of this patent is extended or adjusted under 35 U.S.C. 154(b) by 32 days.

(21) Appl. No.: 14/526,738

(22) Filed: Oct. 29, 2014

(65) Prior Publication Data

US 2015/0140106 A1    May 21, 2015

Related U.S. Application Data

(60) Provisional application No. 61/896,714, filed on Oct. 29, 2013.

(51) Int. Cl.
| | | |
|---|---|---|
| *A61K 9/16* | (2006.01) | |
| *A61K 9/50* | (2006.01) | |
| *A61K 31/727* | (2006.01) | |
| *A61K 9/00* | (2006.01) | |
| *A61K 47/48* | (2006.01) | |
| *A61K 45/06* | (2006.01) | |
| *A61K 9/51* | (2006.01) | |

(52) U.S. Cl.
CPC .......... *A61K 9/5036* (2013.01); *A61K 9/0048* (2013.01); *A61K 9/5026* (2013.01); *A61K 9/5146* (2013.01); *A61K 9/5153* (2013.01); *A61K 9/5161* (2013.01); *A61K 31/727* (2013.01); *A61K 45/06* (2013.01); *A61K 47/4823* (2013.01); *A61K 47/48176* (2013.01)

(58) Field of Classification Search
None
See application file for complete search history.

(56) References Cited

U.S. PATENT DOCUMENTS

| | | | |
|---|---|---|---|
| 8,273,366 B2* | 9/2012 | Chauhan | A61K 9/0048 424/429 |
| 8,668,926 B1* | 3/2014 | Mousa | 424/450 |
| 2005/0113868 A1* | 5/2005 | Devellian | A61B 17/0057 606/213 |
| 2008/0254078 A1* | 10/2008 | Kauper | A61K 9/146 514/1.1 |
| 2009/0186093 A1* | 7/2009 | Liu | A61K 9/5026 424/497 |
| 2009/0220572 A1* | 9/2009 | Deschatelets | A61K 31/00 424/427 |
| 2011/0200673 A1* | 8/2011 | Mousa | A61K 31/727 424/484 |
| 2015/0283254 A1* | 10/2015 | Duvall | A61K 47/48176 424/78.29 |

OTHER PUBLICATIONS

Chakravarthi et al. (International Journal of Pharmaceutics, 2011).*
Phillips et al. (Anticancer Research, 2011).*

* cited by examiner

*Primary Examiner* — Robert A Wax
*Assistant Examiner* — Quanglong Truong
(74) *Attorney, Agent, or Firm* — Schmeiser, Olsen & Watts, LLP (57) ABSTRACT

An ophthalmic formulation that includes nanoparticles. Each nanoparticle includes a shell which encapsulates sulfated non-anticoagulant heparin (SNACH), with or without hydrophobic anti-angiogenesis Tyrosine Kinase inhibitors. The SNACH is ionically or covalently bonded to the shell. The shell includes a polymer selected from the group consisting of poly (lactic-co-glycolic acid) (PLGA), chitosan, chitosan-alginate, and NIPAAM-APMAH-AA, wherein NIPAAM is N-isopropyl acrylamide, APMAH is N-3-aminopropylmethacrylamide hydrochloride, and AA is acrylic acid. A method for treating an eye disease of a subject includes: administering to an eye of the subject a therapeutically effective amount of the ophthalmic formulation for treating the eye disease. The eye disease involves an ocular angiogenesis-mediated disorder.

24 Claims, 4 Drawing Sheets

FIG. 1

FIG. 2
Nanoparticles encapsulating SNACH with or without Hydrophobic anti-angiogenesis (Tyrosine Kinase Inhibitor) average size 50-500 nm and zeta potential from 0 to +30 mv

OCULAR NANOFORMULATION AND METHOD OF USE IN ANGIOGENESIS-MEDIATED DISORDERS

RELATED APPLICATIONS

The present invention claims priority to U.S. Provisional No. 61/896,714, filed on Oct. 29, 2013, which is incorporated herein by reference in its entirety.

TECHNICAL FIELD

The present invention relates to a sustained release and long residing ophthalmic formulation and the process of preparing the same.

BACKGROUND

Most ocular diseases are treated with topical application of solutions administered as eye drops or ointment. One of the major problems encountered with the topical delivery of ophthalmic drugs is the rapid and extensive pre-corneal loss caused by drainage and high tear fluid turn over. After instillation of an eye-drop, typically less than 2-3% of the applied drug penetrates the cornea and reaches the intraocular tissue, while a major fraction of the instilled dose is often absorbed systematically via the conjunctiva and nasolacrimal duct. Another limitation is relatively impermeable corneal barrier that limits ocular absorption.

Ocular drug delivery is an approach to controlling and ultimately optimizing delivery of the drug to its target tissue in the eye. Most of the current formulation efforts aim to maximize ocular drug absorption through prolongation of the drug residence time in the cornea and conjunctival sac as well as to slow drug release from the delivery system and minimizing pre-corneal drug loss. However, most of the current formulation efforts have a blurring effect on vision.

Liposomes have been studied for ocular delivery. However, a limitation of using liposomes for ocular drug delivery is the surface charge of liposomes. Positively charged liposomes seemed to be preferentially captured at the negatively charged corneal surface compared to negatively charged liposomes. Another limitation of liposomes is the instability of the lipid aggregates on the mucine surface.

There have been studies on the use of co-polymeric formulations for delivery of ophthalmic drugs. The pharmaceutical efficacy of these co-polymeric formulations depends on the specific nature and properties of the co-polymeric materials and the compound used. Moreover, the long residence time and sustained release of drug on cornea surface have not been achieved by co-polymeric formulations.

BRIEF SUMMARY

The present invention provides an ophthalmic formulation, comprising: nanoparticles, each nanoparticle comprising a shell which encapsulates sulfated non-anticoagulant heparin (SNACH), wherein the SNACH is ionically or covalently bonded to the shell, wherein the shell comprises a polymer selected from the group consisting of poly(lactic-co-glycolic acid) (PLGA), chitosan, chitosan-alginate, and NIPAAM-APMAH-AA, and wherein NIPAAM is N-isopropyl acrylamide, APMAH is N-3-aminopropylmethacrylamide hydrochloride, and AA is acrylic acid.

The present invention provides a method for treating an eye disease of a subject, said method comprising: administering to an eye of the subject a therapeutically effective amount of the ophthalmic formulation for treating the eye disease, said eye disease involving an ocular angiogenesis-mediated disorder.

DETAILED DESCRIPTION

The present invention obviates drawbacks of the prior art and provides an ophthalmic formulation the includes a nanoparticle formulation containing hydrophobic anti-angiogenesis, and/or anti-inflammatory, compounds such that the nanoparticles have thermosensitivity, mucoadhesiveness, neutral pH, and small particle size all together in a single composition. Nanoparticles as drug carriers for ocular delivery are exceptionally stable and provide a sustained release of an ocular drug. The sustained release can be modulated. The sustained release and long residence time of the ophthalmic formulation of the present invention enables control of release of the drug that is entrapped in the ophthalmic formulation. The entrapped drug may be hydrophobic.

The entrapped drug may be in solution form, in an emulsion, or in powder form. A solvent used for dissolving the drug in a solution may comprise dimethylformamide (DMF), dimethylsulphoxide (DMSO), dichloromethane, ethyl acetate or ethanol.

The ophthalmic formulation may comprise block copolymer micelles which are made of mucoadhesive and thermosensitive polymer components, and when instilled, penetrate the mucine membrane, adhere to the membrane pores and at body temperature, and becomes more hydrophobic to release the drug faster. In order to incorporate one or more of the inventive drugs into the block copolymer micelles, various methods described below may be used alone or in combination.

One method for incorporating one or more of the inventive drugs into the block copolymer micelles utilizes stirring: A drug is added to an aqueous solution of a block copolymer, and stirred for 2 to 24 hours to obtain micelles containing drug.

One method for incorporating one or more of the inventive drugs into the block copolymer micelles utilizes heating: A drug and an aqueous solution of a block copolymer are mixed and stirred at 30 to 80 degree C. for 5 minutes to a couple of hours and then cooled to room temperature while stirring to obtain micelles containing the drug.

One method for incorporating one or more of the inventive drugs into the block copolymer micelles utilizes ultrasonic treatment: A mixture of a drug and an aqueous solution of a block copolymer is subjected to an ultrasonic treatment for 10 minutes to 30 minutes and then stirred at room temperature to obtain micelles containing the drug.

One method for incorporating one or more of the inventive drugs into the block copolymer micelles utilizes solvent evaporation: A drug is dissolved in an organic solvent such as chloroform and then added to an aqueous solution of micelles. Subsequently the organic solvent is evaporated slowly while stirring, and then filtered to remove free drug.

One method for incorporating one or more of the inventive drugs into the block copolymer micelles utilizes dialysis: The polymeric micelles solution is added to an organic solution of drug and the mixture is dialyzed against a buffer solution and then water.

The micelle solution of block copolymers is prepared by dissolving amphiphilic monomers in an aqueous medium to obtain micelles, adding aqueous solutions of cross-linking agent, activator and initiator into the said micelles, subjecting the mixture to polymerization in presence of an inert gas at 30 degree C. to −40 degree C. until the polymerization of micelles is complete.

The purification step is done by dialysis. The dialysis is carried out for 2 to 24 hours, or 2 to 12 hours, to eliminate unreacted monomers and free hydrophobic compound(s), if any, in the aqueous phase. A hydrophobic drug may be incorporated into the polymeric micelles of the present invention during the time of polymerization wherein the drug is dissolved into the micelles of the monomers in aqueous solution and the polymerization is done in presence of the drug. As the drug held in the hydrophobic core of the micelles is released on the cornea surface in a controlled manner for a long time, the composition of the present invention is suitable for formulating drugs, which are not amenable to conventional formulating techniques or using non-mucoadhesive micelles.

Example 1

Design of Nanoparticles Formulation

In initial experiments, three different ophthalmic formulations comprising nanoparticles based on different polymers are prepared. The efficacy of these nanoparticles with different variation of surface charge, size and mucoadhesiveness are examined. Sulfated non-anticoagulant heparin (SNACH) is encapsulated in each of three nanoparticles formulations. Definition: SNACH has a sulfate/carboxylate ratio in a range of greater than 2.4/1 to 3.5/1. The preceding sulfate/carboxylate ratio is a ratio of the number of sulfate groups to the number of carboxylate groups.

Poly(lactic-co-glycolic acid) (PLGA), chitosan and custom made co-polymeric nanoparticles with different ratio of N-isopropyl acrylamide, N-3-aminopropylmethacrylamide hydrochloride, and acrylic acid are synthesized for designing different nanoformulations for SNACH enhanced ocular kinetics. The present invention comprises two different options where the nanoparticles stay on the corneal membrane and deliver SNACH and a third option for increasing nano-uptake across the corneal membrane. The size and surface charge as well as the nature of the nano material may be adjusted to attain optimal eye drop formulation for SNACH.

Figure 1:
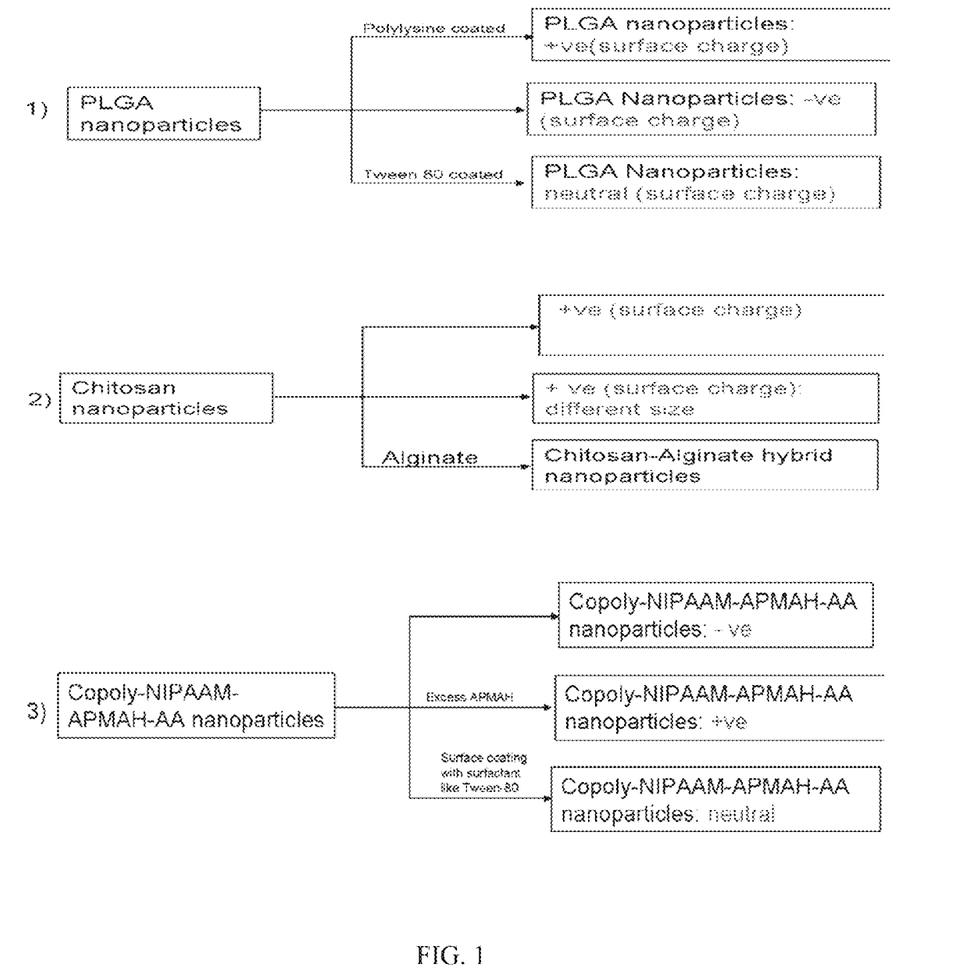
FIG. 1 is a schematic representation showing synthesis of different ophthalmic formulations comprising nanoparticles that encapsulate SNACH and surface modification of the nanoparticles, in accordance with embodiments of the present invention.

FIG. 1 is a schematic diagram showing surface modification of the nanoparticles in different ophthalmic formulations, in accordance with embodiments of the present invention. Each nanoparticle comprises a shell which encapsulates sulfated non-anticoagulant heparin (SNACH), wherein the SNACH is ionically or covalently bonded to the shell, with or without hydrophobic angiogenesis inhibitor from the Tyrosine Kinase inhibitor class such as imatinib, Sunitinib, gefitinib or erlotinib.

FIG. 1 depicts surface modification of the shell of the nanoparticles with respect to whether the shell is positively charged, negatively charged, or electrically neutral.

In a first ophthalmic formulation 1) in FIG. 1: (i) a surface modification of PLGA nanoparticles with a polylysine or chitosan coating results in a positive surface charge of the shell of the PLGA nanoparticles; (ii) no surface modification of PLGA nanoparticles results in a negative surface charge of the shell of the PLGA nanoparticles, and (iii) a surface modification of PLGA nanoparticles with a Tween® 80 coating results in the shell of the PLGA nanoparticles being electrically neutral.

In a second ophthalmic formulation 1) in FIG. 1: no surface modification of chitosan nanoparticles results in a positive surface charge of the shell of the chitosan nanoparticles with either (i) no change in nanoparticle size or (ii) in different nanoparticle sizes; and (iii) addition of alginate to chitosan nanoparticles results in chitosan alginate hybrid nanoparticles.

In a third ophthalmic formulation 1) in FIG. 1: (i) a surface modification of NIPAAM-APMAH-AA nanoparticles with excess APMAH results in a positive surface charge of the shell of the NIPAAM-APMAH-AA nanoparticles; (ii) no surface modification of NIPAAM-APMAH-AA nanoparticles results in a negative surface charge of the shell of the NIPAAM-APMAH-AA nanoparticles, and (iii) a surface modification of PLGA nanoparticles with surfactant such as a Tween® 80 coating results in the shell of the PLGA nanoparticles being electrically neutral, wherein NIPAAM is N-isopropyl acrylamide, APMAH is N-3-aminopropylmethacrylamide hydrochloride, and AA is acrylic acid.

Tween® 80, which is a trademark of Sigma-Aldrich, is identified chemically as either (A) polyoxyethylene (20) sorbitan monooleate; or (B) (x)-sorbitan mono-9-octadecenoate poly (oxy-1,2-ethanediyl).

Figure 2:
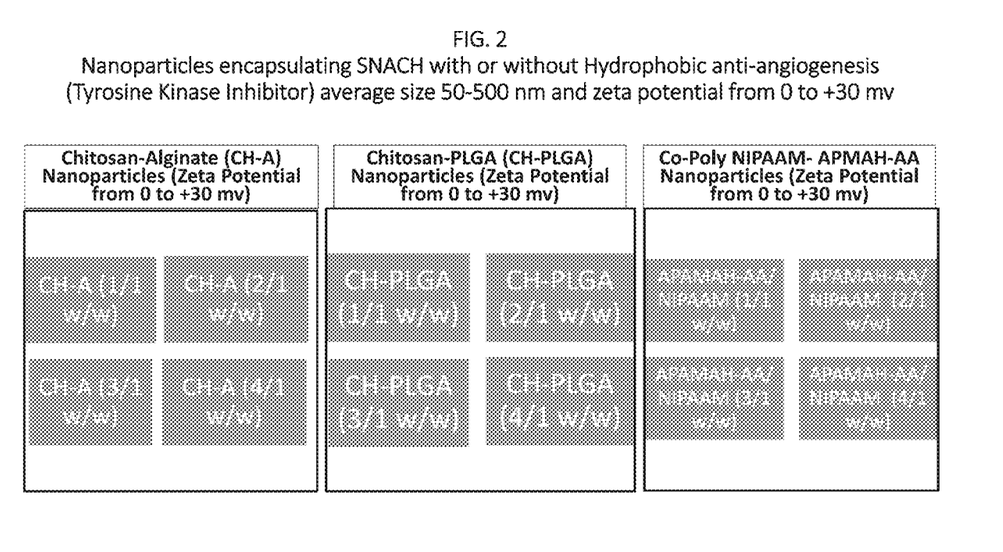
FIG. 2 lists variations in Chitosan-Alginate (CH-A) nanoparticles, Chitosan-PLGA (CH-PLGA) nanoparticles, and NIPAAM-APMAH-AA nanoparticles, in accordance with embodiments of the present invention.

FIG. 2 lists variations in Chitosan-Alginate (CH-A) nanoparticles, Chitosan-PLGA (CH-PLGA) nanoparticles, and NIPAAM-APMAH-AA nanoparticles, in accordance with embodiments of the present invention. FIG. 2 represents a fourth ophthalmic formulation in which the shell comprises Chitosan-Alginate (CH-A), Chitosan-PLGA (CH-PLGA), or NIPAAM-APMAH-AA and in which the shell is positively charged (with a zeta potential in a range of greater than 0 mv to +30 mv) or is electrically neutral (with a zeta potential 0 mv). Thus, the shell of the nanoparticle in FIG. 2 may be positively charged or electrically neutral with a zeta potential ranging from 0 to +30 mv. In one embodiment, the shell of the nanoparticle in FIG. 2 may be positively charged with a zeta potential ranging from +10 to +30 mv. The average size of the nanoparticle in FIG. 2 is on a range of 50 to 500 nm.

The CH-A nanoparticle in FIG. 2 has a CH to A ratio by weight of 1/1, 2/1, 3/1, or 4/1.

The CH-PLGA nanoparticle in FIG. 2 has a CH to PLGA ratio by weight of 1/1, 2/1, 3/1, or 4/1.

The NIPAAM-APMAH-AA nanoparticle in FIG. 2 has a APMAH-AA to NIPAAM ratio by weight of 1/1, 2/1, 3/1, or 4/1.

Example 2

Analysis of Nanoparticles

Based on the original method developed by PRI a modified HPLC analytical method specific for SNACH nanoparticles was developed. Development of analytical method for indirect quantitation of SNACH inside the nanoparticles is also on agenda. From a set, half of the total amount of the nanoparticles were disintegrated in 50% acetone and analyzed directly by HPLC for total amount of free and encapsulated SNACH. On the other hand, the other half of nanoparticles were filtered through a 100 KD centrifugal filter membrane device, and the filtrate were analyzed by HPLC for the total amount of free SNACH. Thus, the difference between the amounts of SNACH in the two analyses would represent the amount of SNACH inside the nanoparticles. The sample preparation protocol would have to be tested for each kind of nanoparticles, and adjusted accordingly.

Example 3

In Vitro Release Kinetics

To study the release kinetics, a known amount of the nanoparticles formulation encapsulating SNACH were suspended in desired medium in which the release kinetics are to be studied. The solution were distributed as 500 ul aliquots in micro-centrifuge tubes. At predetermined intervals of time the solutions were filtered through centrifugal filter membrane device (100 KD cut off) as indicated above to separate free SNACH from the loaded nanoparticles. The concentration of free SNACH were determined by HPLC. % Release=$([SNACH]_{f,t})/([SNACH]_0) \times 100$, wherein $[SNACH]_{f,t}$ is the concentration of SNACH in the filtrate at time t. $[SNACH]_0$ is the total amount of the encapsulated SNACH.

Example 4

In Vivo Experiments

Preliminary in vivo experiments were performed to test the efficacy of the nanoparticles formulations in New Zealand White rabbits' eyes as compared to a control of the drug without nanoparticles. The procedure of application, collection method of the aqueous humor etc. were described in details in the animal protocol. The remaining portion of each eye were saved and stored frozen at −80° C. for possible future analysis. Four eyes from two rabbits were used for each formulation at each testing point (n=4). Aqueous humor samples were collected at 30 and 90 minutes after topical drug administration, where two animals were sacrificed for each time point. Samples from aqueous humor collected were frozen at −80° C. until the time of analysis if necessary.

All samples were analyzed by HPLC. The new specific method for analysis of SNACH in Nanoparticles were used for analyzing SNACH, both free and encapsulated. Filtration of the aqueous humor through 100 KD filters were used as described earlier to study the two forms of SNACH.

Example 5

Chick Chorioallantoic Membrane (CAM) Model of Angiogenesis

The effect of SNACH on Neovascularization-mediated by VEGF+FGF2 was examined in the CAM model. Briefly, ten-day old chick embryos were purchased from Spafas, Inc. (Preston, Conn.) and incubated at 37° C. with 55% relative humidity. A hypodermic needle was used to make a small hole in the shell at the air sac and a second hole will be made on the broadside of the egg, directly over an avascular portion of the embryonic membrane that will be identified by candling. A false air sac was created beneath the second hole by the application of negative pressure at the first hole, causing the CAM to separate from the shell. A window, approximately 1.0 cm$^2$, was cut in the shell over the dropped CAM with a small crafts grinding wheel (Dremel, Division of Emerson Electric Co., Racine, Wis.), allowing direct access to the underlying CAM. VEGF and FGF2 at 1 µg/ml each was used as a standard pro-angiogenic agent to induce new blood vessel branches on the CAM of the 10-day old embryos. Sterile disks of #1 filter paper (Whatman International, United Kingdom) were pre-treated with 3 mg/ml cortisone acetate and air dried under sterile conditions. SNACH was dissolved in PBS and tested at 2 ug/CAM. Filters treated VEGF and FGF2 were placed on the first day of the 3-day incubation, with SNACH added 30 min later at 2.0 ug/CAM as indicated above.

Microscopic analysis of CAM sections was performed. After incubation at 37° C. with 55% relative humidity for 3 days, the CAM tissue directly beneath each filter disk were resected from control and treated CAM samples. Tissues were washed 3 times with PBS, placed in 35-mm Petri dishes (Nalge Nunc, Rochester, N.Y.) and examined under an SV6 stereomicroscope (Karl Zeiss, Thornwood, N.Y.) at 50× magnification. Digital images of CAM sections exposed to filters were collected, using a 3-CCD color video camera system (Toshiba America, New York, N.Y.), and analyzed with Image-Pro software (Media Cybernetics, Silver Spring, Md.). The numbers of vessel branch points contained in a circular region equal to the area of each filter disk were counted. One image were counted in each CAM preparation, and findings from 6-8 CAM preparations/group were analyzed for each treatment condition.

Figure 3:
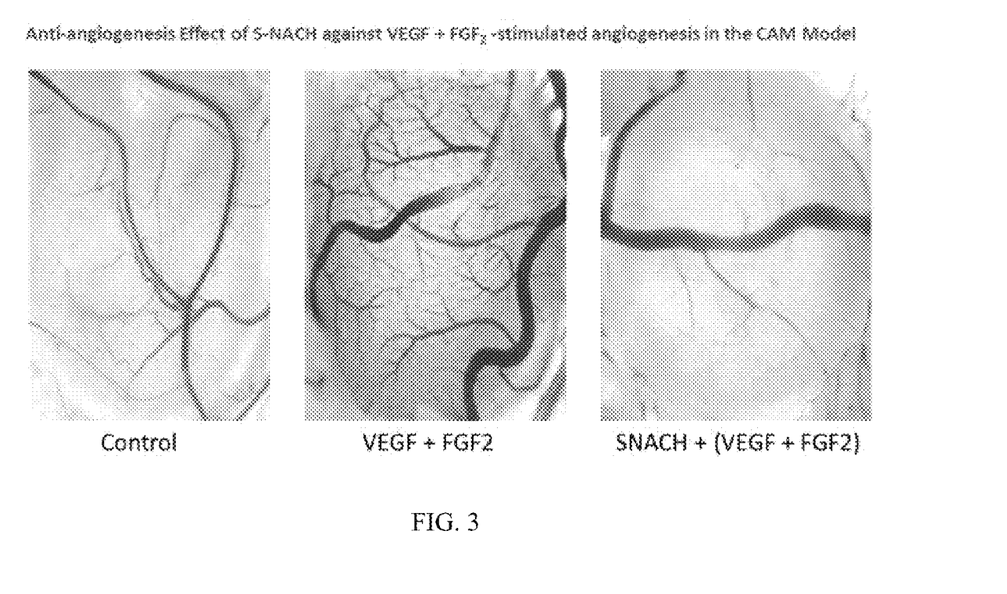
FIG. 3 is a representative images of growth factors (VEGF+FGF2)-mediated neovascularization (angiogenesis) in the CAM model and its maximal inhibition by SNACH treatment, in accordance with embodiments of the present invention.

FIG. 3 is representative images illustrating the potent stimulation of angiogenesis by VEGF+FGF2 as compared to control (PBS), while SNACH treatment with VEGF+FGF2 demonstrated maximal inhibition of angiogenesis-induced by VEGF and FGF2, in accordance with embodiments of the present invention.

Example 6

Efficacy of SNACH and SNACH Nanoparticles in Retinal Neovascularization in Infant Mice with Retinopathy of Prematurity (ROP)

Retinopathy of Prematurity (ROP) is a blindness-causing neovascularizing disease affecting premature infants treated with high concentrations of oxygen. ROP develops in two distinct stages: 1) the hyperoxic insult leads to obliteration of immature retinal vessels and 2) initiated upon resumption of the breathing of normal air, is an adverse compensatory neovascularization response. The formation of new vessels is excessive, neovessels are leaky, and the inner limiting membrane of the retina is breached, allowing vessel growth into the vitreous which might ultimately lead to retinal detachment and vision loss. The formation of new vessels is mediated by ischemia-induced vascular endothelial growth factor (VEGF). See Keshet, E. (2003), "Preventing pathological regression of blood vessels", J. Clin. Invest. 112(1), 27-29.

VEGF is a potent and specific endothelial cell cytokine that can be up-regulated by hypoxia. Evidences show that VEGF is a significant mediator in retinal neovascular diseases and other disorders in which hypoxia is believed to influence the pathogenesis. See Robbins S G, C. J., Ford B L, Roberto K A, Penn J S. (1997), "Detection of vascular endothelial growth factor (VEGF) protein in vascular and non-vascular cells of the normal and oxygen-injured rat retina", Growth Factors 14(4): 229-241.

The formulation of S-NACH Chitosan Nanoparticles formulation was lyophilized and suspended in physiological saline as needed.

a) Formulation and Dosing:

SNACH and SNACH Nanoparticles (1 mg/kg) in PBS at pH 7-7.5, Control: PBS at 1 mg/ml on postnatal day 12 and 15, Mode of Administration: Intraperitoneal or eye drops. This nanoformulation showed longer residence time on the cornea allowing for greater permeation of SNACH or its SNACH chitosan Nanoparticles.

An animal model of a mice model was used. The mice model used was the Oxygen-induced retinopathy mouse model as described by Smith L E, W. E., McLellan A, Kostyk S K, D'Amato R, Sullivan R, D'Amore P A. (1994), "Oxygen-induced retinopathy in the mouse", Invest Ophthalmol Vis Sci 35(1): 101-111.

The neonatal mice were exposed to hyperoxic conditions for 5 days, beginning at age p7 for the pups and continuing through p12 when they are returned to normal oxygen atmosphere (8-10 animals/group). Treatment group SNACH at 1 mg/kg administered IP or eye drops at two separate doses one at P12 and the other at P15. Day 17 animals were scarified and eyes removed for retinal Neovascularization evaluation. The removed eyes were stained with H&E stain. Additionally in upcoming study 3 additional animals per group were used for ocular tissue levels of SNACH after SNACH administration by LC/MS/MS.

Induction of oxygen-induced retinopathy in mouse model, in accordance with embodiments of the present invention. Immunohistochemical staining of ROP mice indicating normal vessels in the eye at room air, capillary drop out due to decrease in VEGF and other angiogenic factors at O2: 75±2% and neovascularization due to increase in VEGF and other angiogenic factors when the mice were brought back to room air.

Figure 4:
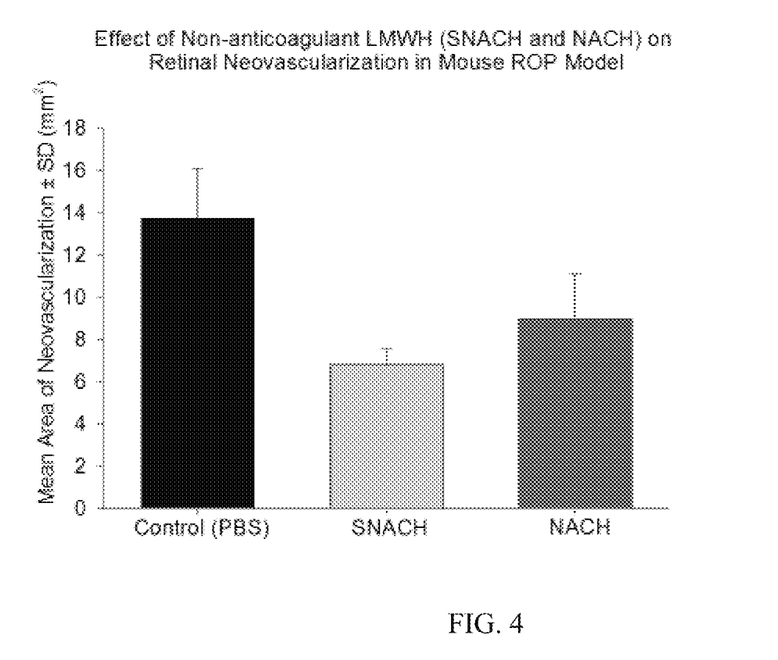
FIG. 4 depicts the effective inhibition of retinal neovascularization in the neonatal mouse model by SNACH (60-70% inhibition) and NACH (50% inhibition), in accordance with embodiments of the present invention.

FIG. 4 includes data representing mean total area of neovascularization after the administration of SNACH at 1.0 mg/kg, IP on day 12 and 15, in accordance with embodiments of the present invention. SNACH resulted in about 60-70% inhibition of neovascularization, while NACH resulted in about 50% inhibition of retinal neovascularization.

Various anti-VEGF pharmacotherapies have been developed to address the neovascular AMD, including pegaptanib sodium (Macugen, OSI/Eyetech), ranibizumab (Lucentis, Genentech), and bevacizumab. Of these, Phase 3 clinical trials of ranibizumab for wet AMD have demonstrated the regression of choroidal neovascular membranes while Intravitreal injection of bevacizumab for the treatment of ROP resulted in regression of neovascularization secondary to ROP. See Lalwani G, B. M., Cardone S, Murray T G, and B. Puliafito C A, A M (2007), "Bevacizumab for Salvage Treatment in Threshold Retinopathy of Prematurity", Retinal Physician.

Along these lines it is interesting to note that SNACH, a potent angiogenesis inhibitors of VEGF, bFGF or other growth factors as shown in the CAM model, causes neovascular regression in ROP mice model. Thus it can be concluded that SNACH or its nanoformulation could play an important role in eye diseases involving neovascularization.

Example 7

Preparation of SNACH

Definition: sulfated non-anticoagulant heparin (NACH) has a sulfate/carboxylate ratio in a range of greater than 1.5 to 2.4/1, sulfated non-anticoagulant heparin (SNACH) has a sulfate/carboxylate ratio in a range of greater than 2.4/1 to 3.5/1, and super-sulfated non-anticoagulant heparin (S-SNACH) has a sulfate/carboxylate ratio in a range of greater than 3.5/1 to 5.0/1.

Preparation of different molecular sizes of Low Molecular Weight Heparin (LMWH) starts from unfractionated heparin, which is subjected to either enzymatic depolymerization using heparinase (generating LMWH with Molecular weight ranging from 6,000-,8,000 Dalton) or by chemical depolymerization using Nitrous Oxide (generating LMWH with Molecular weight ranging from 4,000-6,000 Dalton). The Generated LMWHs with different sizes are subjected periodate oxidation to open the sugar ring within the pentasaccharide, which results in the loss of binding to anti-thrombin III and hence the anti-Xa and anti-IIa activities. This is followed by either column separation of the non-anticoagulant LMWH (NACH) species with the different sulfation ranges as stated above or the final NACH product is subjected to chemical or enzymatic sulfation to achieve the above ranges for SNACH or S-SNACH.

Example 8

Examples of Hydrophobic SNACH Derivatives

SNACH is hydrophilic and to prepare hydrophobic SNACH, either ionic complex or covalent binding was carried out, to mask the polyanionic charges for improved permeation across the intestinal barriers, using fatty acids (eicosapentaenoic acid (EPA), docosahexaenoic acid (DHA), or other fatty acids) to complex with SNACH via its NH2, amino acids to complex with SNACH via its COOH or NH2 or polymers with carboxyl terminal such as PLGA to complex with SNACH via its NH2 or alcohol such PEG or PVA to complex with SNACH via its COOH.

Example 9

Enablement for Forming the Surface Charges and Particle Size of Nanoparticles in FIG. 1

As under by complexing with the SNACH via its COO— group that form the polyanionic charges using Chitosan-fatty acid complex (DHA-CA) forming a hydrophobic SNACH at DHA-CA/SNACH 1/1 (w/w) ratio, which can form DHA-Chitosan nanoparticles or using SNACH/DHA-CA at 3-5/1 (w/w) ratio and then encapsulate into PLGA nanoparticles coated with deoxycholate with particles size ranging from 50-500 nm and zeta potential ranging from 0 to +30 mv.

Example 10

Description of Thermo-Sensitive Properties Provided by NIPAAM

Among the various temperature-sensitive polymers utilized by the inventor of the present invention, poly (N-isopropylacrylamide) [poly (NIPAAM)] is employed as a core or shell in the forms of particle and gel. Generally, poly (NIPAAM) exhibits a hairy structure below the lower critical solution temperature (LCST) and undergoes hydrophobic aggregation above the LCST due to a change in hydrogen bonding between water and amide groups of poly (NIPAAM). Therefore, particles consisting of poly (NIPAAM) show a unique conformational behavior with respect to environmental temperature, eventually allowing for the thermosensitive drug release.

Example 11

Description of pH-Sensitive Properties

Hydrogels based on NIPAAM and DMAEMA were prepared via free radical polymerization. The resulting P (NIPAAM-co-DMAEMA) hydrogels were characterized in terms of swelling kinetics, temperature response kinetics, and effect of pH. The formed P (NIPAAM-co-DMAEMA) hydrogels have the strong sensitivity in term of release kinetic of encapsulated SNACH to external temperature and pH. Importantly, the incorporation of DMAEMA moiety not only provides the pH sensitivity, but also maintains the thermal properties of P (NIPAAM-co-DMAEMA) hydrogels even at low molar ratios of DMAEMA as low as 15%.

The present invention provides an ophthalmic formulation, comprising nanoparticles, wherein each nanoparticle comprises a shell which encapsulates sulfated non-anticoagulant heparin (SNACH). The SNACH is ionically or covalently bonded to the shell. The shell is positively charged or electrically neutral. The shell comprises a polymer selected from the group consisting of poly (lactic-co-glycolic acid) (PLGA), chitosan, chitosan-alginate, and NIPAAM-APMAH-AA, wherein NIPAAM is N-isopropyl acrylamide, APMAH is N-3-aminopropylmethacrylamide hydrochloride, and AA is acrylic acid.

In one embodiment, the shell encapsulates a hydrophobic anti-angiogenesis agent. In one embodiment, the hydrophobic anti-angiogenesis agent comprises a tyrosine kinase inhibitor, an anti-vascular endothelial growth factor, or a combination thereof. In one embodiment, the tyrosine kinase inhibitor is imatinib, Sunitinib, gefitinib or erlotinib.

In one embodiment, each nanoparticle comprises a diameter in a range of 50 nanometers to 500 nanometers.

In one embodiment, the shell comprises PLGA by bridging it with higher levels of Chitosan and is positively charged.

In one embodiment, the shell comprises PLGA by bridging with lower levels of Chitosan or 1/1 (w/w) and is electrically neutral.

In one embodiment, the shell comprises chitosan and is positively charged with a zeta potential ranging from 10 to +30 mv.

In one embodiment, the shell comprises chitosan-alginate.

In one embodiment, the shell comprises NIPAAM-APMAH-AA and is positively charged (+10 to +30 mv zeta potential).

In one embodiment, the shell comprises NIPAAM-APMAH-AA and is positively charged or electrically neutral with a zeta potential ranging from 0 to +30 mv.

In one embodiment, the ophthalmic formulation comprises an emulsion, and wherein the emulsion comprises the nanoparticles dispersed in a liquid. In one embodiment, the ophthalmic formulation comprises an eye drop that includes the emulsion, wherein the eye drop is configured to be applied to an eye of a subject to treat the subject for an eye disease involving an ocular angiogenesis-mediated disorder.

In one embodiment, the ophthalmic formulation is an ointment that includes the nanoparticles, wherein the ointment is configured to be applied to an eye of a subject to treat the subject for an eye disease involving an ocular angiogenesis-mediated disorder.

In one embodiment, the polymer comprises a copolymer such as block copolymer.

In one embodiment, the block copolymer polymer provides thermo-sensitivity properties derived from N-Isopropyl acrylamide (NIPAAM).

In one embodiment, a monomer that may be utilized to provide hydrogel formulation properties of the copolymer to reduce the irritability of the eye is selected from a vinyl group of compounds that may include vinyl pyrrolidone, vinyl alcohol, vinyl chloride, or vinyl acetate.

In one embodiment, a monomer that may be utilized to provide thermo-sensitivity properties of the block copolymer are biocompatible and non-antigenic materials.

In one embodiment, a monomer that may be utilized to provide mucoadhesiveness and pH-sensitivity properties to the copolymer and is selected from acrylate based monomers. The mucoadhesiveness and pH-sensitivity properties may be achieved by subjecting the resulting mixture to stirring, heating, ultrasonic treatment, solvent evaporation or dialysis to physically incorporate the hydrophobic drug into the hydrophobic core of co-polymeric micelle; and purifying the mixture to recover the sustained release and long residing ophthalmic formulation.

In one embodiment, the block copolymers, made of amphiphilic monomers, are biocompatible and non-antigenic materials.

The present invention provides a method for treating an eye disease of a subject, wherein the method comprises administering to an eye of the subject a therapeutically effective amount of the ophthalmic formulation of the present invention for treating the eye disease, said eye disease involving an ocular angiogenesis-mediated disorder. The subject may be a mammal. The subject may be a human being. The method achieves a sustained release and a long residing time of the ophthalmic formulation and may use bonding types (e.g., ionic binding, covalent bonding) to control the rate of release of SNACH and other bioactive hydrophobic compounds (e.g., tyrosine kinase inhibitors) encapsulated within the shell of the nanoparticle.

In one embodiment, the eye disease is selected from the group consisting of retinopathy of prematurity (ROP), diabetic retinopathy (DR), age-related macular degeneration (AMD), and combinations thereof.

In one embodiment, the ophthalmic formulation comprises an eye drop that includes an emulsion, wherein the emulsion comprises the nanoparticles dispersed in a liquid, wherein administering the ophthalmic formulation to an eye of the patient comprises applying the eye drop to the eye of the patient.

In one embodiment, the ophthalmic formulation comprises an ointment that includes the nanoparticles, wherein administering the ophthalmic formulation to an eye of the patient comprises applying the ointment to the eye of the patient.

In one embodiment, forming the ophthalmic formulation may include dissolving the hydrophobic drug in a solvent selected from the group consisting of dimethylformamide (DMF), dimethylsulphoxide (DMSO), ethyl acetate, ethanol, and other dialyzable solvents.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. An ophthalmic formulation, comprising:
nanoparticles, each nanoparticle comprising a shell which encapsulates sulfated non-anticoagulant heparin (SNACH), wherein the SNACH is ionically or covalently bonded to the shell, wherein the shell comprises a polymer selected from the group consisting of poly (lactic-co-glycolic acid) (PLGA), chitosan, chitosan-alginate, and NIPAAM-APMAH-AA, wherein NIPAAM is N-isopropyl acrylamide, wherein APMAH is N-3-aminopropylmethacrylamide hydrochloride, and wherein AA is acrylic acid.

2. The ophthalmic formulation of claim 1, wherein the shell further encapsulates a hydrophobic anti-angiogenesis agent.

3. The ophthalmic formulation of claim 2, wherein the hydrophobic anti-angiogenesis agent comprises a tyrosine kinase inhibitor, an anti-vascular endothelial growth factor, or a combination thereof.

4. The ophthalmic formulation of claim 1, wherein each nanoparticle comprises a diameter in a range of greater than 200 nanometers to 500 nanometers.

5. The ophthalmic formulation of claim 1, wherein the SNACH is ionically bonded to the shell.

6. The ophthalmic formulation of claim 1, wherein the SNACH is covalently bonded to the shell.

7. The ophthalmic formulation of claim 1, wherein the shell is positively charged with a zeta potential ranging from 10 to 30 mv.

8. The ophthalmic formulation of claim 1, wherein the shell is negatively charged.

9. The ophthalmic formulation of claim 1, wherein the shell is electrically neutral.

10. The ophthalmic formulation of claim 1, wherein the shell comprises Chitosan-PLGA and is positively charged or electrically neutral with a zeta potential ranging from 0 to 30 mv.

11. The ophthalmic formulation of claim 1, wherein the shell comprises Chitosan-PLGA and is electrically neutral with a zeta potential of 0 mv.

12. The ophthalmic formulation of claim 1, wherein the shell comprises chitosan and is positively charged with a zeta potential ranging from 10 to 30 mv.

13. The ophthalmic formulation of claim 1, wherein the shell comprises chitosan-alginate.

14. The ophthalmic formulation of claim 1, wherein the shell comprises NIPAAM-APMAH-AA and is positively charged with a zeta potential ranging from 0 to 30 mv.

15. The ophthalmic formulation of claim 1, wherein the shell comprises NIPAAM-APMAH-AA and is electrically neutral.

16. The ophthalmic formulation of claim 1, wherein the ophthalmic formulation comprises an emulsion, and wherein the emulsion comprises the nanoparticles dispersed in a liquid.

17. The ophthalmic formulation of claim 16, wherein the ophthalmic formulation comprises an eye drop that includes the emulsion, and wherein the eye drop is configured to be applied to an eye of a subject to treat the subject for an eye disease involving an ocular angiogenesis-mediated disorder.

18. The ophthalmic formulation of claim 1, wherein the ophthalmic formulation is an ointment that includes the nanoparticles, and wherein the ointment is configured to be applied to an eye of a subject to treat the subject for an eye disease involving an ocular angiogenesis-mediated disorder.

19. A method for treating an eye disease of a subject, said method comprising:
administering to an eye of the subject a therapeutically effective amount of the ophthalmic formulation of claim 1 for treating the eye disease, said eye disease involving an ocular angiogenesis-mediated disorder.

20. The method of claim 19, wherein the eye disease is selected from the group consisting of retinopathy of prematurity (ROP), diabetic retinopathy (DR), age-related macular degeneration (AMD), and combinations thereof.

21. The method of claim 19, wherein the ophthalmic formulation comprises an eye drop that includes an emulsion, wherein the emulsion comprises the nanoparticles dispersed in a liquid, and wherein said administering comprises applying the eye drop to the eye of the patient.

22. The method of claim 19, wherein the ophthalmic formulation comprises an ointment that includes the nanoparticles, and wherein said administering comprises applying the ointment to the eye of the patient.

23. The method of claim 19, wherein the subject is a human being.

24. The method of claim 16, wherein the subject is a mammal.

* * * * *